United States Patent
Notoya et al.

(10) Patent No.: US 10,947,585 B2
(45) Date of Patent: Mar. 16, 2021

(54) NUCLEIC ACID AMPLIFICATION METHOD PRODUCING URACIL-CONTAINING AMPLIFICATION PRODUCTS

(71) Applicant: SYSMEX CORPORATION, Kobe (JP)

(72) Inventors: Michitaka Notoya, Kobe (JP); Shuji Yamashita, Kobe (JP); Mika Yoshimura, Kobe (JP); Yutaka Maeda, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 269 days.

(21) Appl. No.: 15/900,942

(22) Filed: Feb. 21, 2018

(65) Prior Publication Data

US 2018/0245145 A1   Aug. 30, 2018

(30) Foreign Application Priority Data

Feb. 24, 2017   (JP) .............................. JP2017-033886

(51) Int. Cl.
  *C12Q 1/6848*   (2018.01)
  *C12Q 1/686*   (2018.01)

(52) U.S. Cl.
  CPC ........... *C12Q 1/6848* (2013.01); *C12Q 1/686* (2013.01)

(58) Field of Classification Search
  CPC ............................. C12Q 1/6848; C12Q 1/686; C12Q 2525/101; C12Q 2537/149
  See application file for complete search history.

(56) References Cited

U.S. PATENT DOCUMENTS

| 7,687,247 B1 | 3/2010 | Hartley et al. | |
| 2010/0129874 A1* | 5/2010 | Mitra | C12P 19/34 435/91.2 |
| 2012/0237943 A1* | 9/2012 | Soldatov | C12Q 1/6853 435/6.19 |
| 2016/0340746 A1* | 11/2016 | Makarov | C12Q 1/6869 |

FOREIGN PATENT DOCUMENTS

GB   2293238 A   *   3/1996   ........... C12Q 1/6848

OTHER PUBLICATIONS

Meyer, M. & Kircher, M. Illumina Sequencing Library Preparation for Highly Multiplexed Target Capture and Sequencing. Cold Spring Harbor Protocols; 2010; doi:10.1101/pdb.prot5448 (Year: 2010).*
Aslanzaden, J. Preventing PCR Amplification Carryover Contamination in a Clinical Laboratory. Annals of Clinical & Laboratory Science 2004; 34: 389-396 (Year: 2004).*
Loewe, R.P. Combinational usage of next generation sequencing and qPCR for the analysis of tumor samples. Methods 2013; 59: 126-131 (Year: 2013).*
Zhu et al. Single-molecule emulsion PCR in microfluidic droplets. Analytical and Bioanalytical Chemistry 2012; 403: 2127-2143 (Year: 2012).*
Frank Diehl, et al, "BEAMing: single-molecule PCR on microparticles in water-in-oil emulsions", Nature Methods, Jul. 2006, pp. 551-559, vol. 3, No. 7.
Roger S. Lasken, et al., "Archaebacterial DNA Polymerases Tightly Bind Uracil-containing DNA", The Journal of Biological Chemistry, Jul. 1996, pp. 17692-17696, vol. 271, No. 30.
Josephine Wardle, et al., "Uracil recognition by replicative DNA polymerases is limited to the archea, not occurring with bacteria and eukarya", Nucleic Acids Research, 2008, pp. 705-711, vol. 36, No. 3.
Communication, dated Jan. 4, 2021, issued by the Japanese Patent Office in Japanese Patent Application No. 2017-033886.

* cited by examiner

*Primary Examiner* — Angela M. Bertagna
(74) *Attorney, Agent, or Firm* — Sughrue Mion, PLLC

(57)   ABSTRACT

Disclosed is a nucleic acid amplification method. The method comprises: performing a first nucleic acid amplification using a target nucleic acid contained in a sample as a template; and performing a second nucleic acid amplification using the amplification product produced in the first nucleic acid amplification step as a template. In the first nucleic acid amplification, a DNA polymerase that selectively amplifies a nucleic acid not comprising a uracil base is used to produce an amplification product that does not comprise a uracil base. In the second nucleic acid amplification, (i) dUTP and/or a primer comprising a uracil base, and (ii) a DNA polymerase capable of amplifying a nucleic acid comprising a uracil base are used to produce an amplification product that comprises a uracil base.

19 Claims, 3 Drawing Sheets

Specification includes a Sequence Listing.

NUCLEIC ACID AMPLIFICATION METHOD PRODUCING URACIL-CONTAINING AMPLIFICATION PRODUCTS

CROSS REFERENCE TO RELATED APPLICATIONS

This application claims priority from prior Japanese Patent Application No. 2017-033886, filed on Feb. 24, 2017, entitled "NUCLEIC ACID AMPLIFICATION METHOD", the entire contents of which are incorporated herein by reference.

TECHNICAL FIELD

The present invention relates to a nucleic acid amplification method.

BACKGROUND

Since the nucleic acid amplification apparatus is repeatedly used, there is a problem that false positive may occur because the amplification product after nucleic acid amplification is mixed into a reaction solution of the following nucleic acid amplification. This is generally called a carryover, and a method described in U.S. Pat. No. 7,687,247 is known as a technique for suppressing the carryover.

U.S. Pat. No. 7,687,247 describes a method comprising the steps of producing an amplification product containing a uracil base in an amplification step of a nucleic acid, and treating the amplification product with an enzyme that degrades a nucleic acid containing a uracil base before performing the following nucleic acid amplification to degrade the amplification product containing a uracil base of the previous nucleic acid amplification.

In the case where DNA is used as a template, a nucleic acid containing a uracil base mixed due to carryover is degraded, and the template nucleic acid is amplified, according to this method.

SUMMARY

The scope of the present invention is defined solely by the appended claims, and is not affected to any degree by the statements within this summary.

According to the present invention, there is provided a nucleic acid amplification method.

The method comprises the steps of performing a first nucleic acid amplification using a target nucleic acid contained in a sample as a template, and performing a second nucleic acid amplification using the amplification product produced in the first nucleic acid amplification step as a template.

In the first nucleic acid amplification, a DNA polymerase that selectively amplifies a nucleic acid not comprising a uracil base is used to produce an amplification product that does not comprise a uracil base. In the second nucleic acid amplification, (i) dUTP and/or a primer comprising a uracil base, and (ii) a DNA polymerase capable of amplifying a nucleic acid comprising a uracil base are used to produce an amplification product that comprises a uracil base.

DETAILED DESCRIPTION OF THE PREFERRED EMBODIMENTS

Figure 1A:
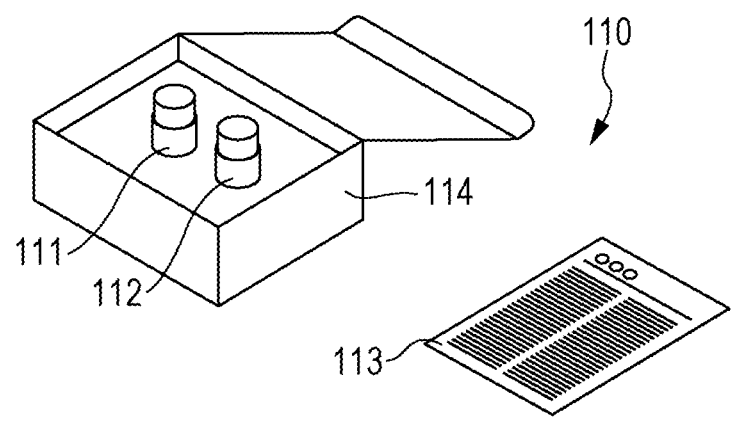
FIG. 1A is a diagram showing an example of the external appearance of a reagent of the present embodiment.

In the present embodiment, a nucleic acid amplification method in which the effect of carryover is suppressed is provided by obtaining a large excess of the target nucleic acid amplification product (first nucleic acid amplification product) as compared with the carryover nucleic acid and performing the second nucleic acid amplification using the first nucleic acid amplification product as a template.

In the present embodiment, at least two nucleic acid amplification steps, "first nucleic acid amplification step" and "second nucleic acid amplification step", are performed. In the second nucleic acid amplification step, a nucleic acid amplification reaction is performed by adding a new amplification reagent (polymerase or dNTPs) to a part or all of the reaction solution containing the amplification product of the first nucleic acid amplification step.

Usually, the second nucleic acid amplification step is performed in a container different from the container used in the first nucleic acid amplification step. The aspects of the first nucleic acid amplification step and the second nucleic acid amplification step are not particularly limited. In particular, the method of this embodiment is suitable for performing two-stage PCR, like a combination of multiplex PCR and singleplex PCR, pre-amplification and emulsion PCR in the BEAMing method (Diehl, et al. Nature Methods vol. 3, No. 7, July 2006, 551-9), nested PCR, and the like.

The nucleic acid amplification method of the present embodiment includes a step of performing first nucleic acid amplification using a target nucleic acid contained in a sample as a template. In this first nucleic acid amplification step, a DNA polymerase that selectively amplifies a nucleic acid not containing a uracil base is used to produce an amplification product not containing a uracil base.

The sample is not particularly limited as long as it contains a target nucleic acid, and examples thereof include biological samples derived from animals including human, plants, microorganisms and the like, nucleic acid-containing samples for experiments, samples that can contain a nucleic acid, like viruses, foods, biological preparations, soil, waste water, and the like. The biological sample is not particularly limited, and examples thereof include human blood (whole blood), plasma, serum, urine, feces, sputum, tears, saliva, washing liquid, bone marrow, other body fluids, and the like. The sample may be a solid tissue. The sample may be treated with an appropriate agent prior to analysis, as necessary.

The sample may be diluted with an aqueous medium as necessary, for adjustment of the concentration of the target nucleic acid to be described later or the like. Examples of such aqueous medium include water, phosphate buffer solutions, physiological saline solutions, and the like.

The target nucleic acid is not particularly limited as long as it is deoxyribonucleic acid (DNA), and examples thereof include genomic DNA, cDNA, PCR product of genomic DNA, PCR product of cDNA, synthetic polynucleotide, and the like. The target nucleic acid may be of human origin. The target nucleic acid may be derived from other eukaryotes, for example, animals or plants, prokaryotes or viruses.

The size of the target nucleic acid is not particularly limited. When a target nucleic acid contained in a sample is used as a template, the target nucleic acid is preferably 300 bp or less, more preferably 200 bp or less, and further preferably 200 bp or less and 30 bp or more.

The form of the target nucleic acid is not particularly limited. The form of the target nucleic acid may be a linear or circular nucleic acid. The form of the target nucleic acid may be a single-stranded or double-stranded nucleic acid.

The reaction solution for the first nucleic acid amplification preferably contains a sample containing a target nucleic acid as a template, dATP, dTTP, dCTP and dGTP, a DNA polymerase that selectively amplifies a nucleic acid not containing a uracil base, and first and second primers.

The DNA polymerase that selectively amplifies a nucleic acid not containing a uracil base is preferably a DNA polymerase derived from archaebacteria, more preferably a thermostable DNA polymerase derived from *Pyrococcus* or derived from *Thermococcus kodakaraensis*, and further preferably Phusion™ Hot Start High-Fidelity DNA Polymerase and/or KOD plus neo. Here, the phrase "selectively amplifies a nucleic acid not containing a uracil base" refers to that does not substantially amplify a nucleic acid containing a uracil base while amplifying a nucleic acid not containing a uracil base. The phrase "does not substantially amplifying a nucleic acid not containing a uracil base" means that a nucleic acid not containing a uracil base can be amplified within a range not to adversely affect the implementation of the method of the present embodiment.

The concentration of the DNA polymerase that selectively amplifies a nucleic acid not containing a uracil base in the reaction solution for the first nucleic acid amplification is preferably 0.01 to 0.2 unit/1 µl, and more preferably 0.02 to 0.1 unit/100 µl.

The concentrations of dATP, dTTP, dCTP and dGTP in the reaction solution for the first nucleic acid amplification are preferably 0.1 to 0.4 µM, and more preferably 0.2 to 0.25 µM, respectively. The reaction solution is preferably a liquid sample in which dUTP is not substantially present and a nucleic acid containing a uracil base may be present due to carryover. The phrase "dUTP is not substantially present" means that dUTP may be present within a range not to adversely affect the implementation of the method of the present embodiment. The phrase "a nucleic acid containing a uracil base may be present" in the reaction solution for the first nucleic acid amplification means that, for example, a second nucleic acid amplification product containing a uracil base derived from other samples may be contained in the reaction solution as a carryover nucleic acid.

The method of the present embodiment does not necessarily require a step of degrading a nucleic acid containing a uracil base. The step of degrading a nucleic acid containing a uracil base is a degradation step by UDG as described in, for example, U.S. Pat. No. 7,687,247.

The first and second primers used in the first nucleic acid amplification are not particularly limited as long as they are oligonucleotides that hybridize to a partial region of the target nucleic acid under stringent conditions and can be used in nucleic acid amplification. The first and second primers can be appropriately designed by those skilled in the art, in consideration of the relationship between third and fourth primers used in the following second nucleic acid amplification step. The stringent conditions mean the conditions that the primer can specifically hybridize to the template nucleic acid, when there is at least 90% and preferably at least 95% sequence identity between the primer and the template nucleic acid. Generally, stringent conditions are set to be about 5° C. lower than the thermal melting point (Tm) of a given base sequence at a defined ionic strength and pH. This Tm is the temperature at which 50% of the primers complementary to the base sequence of the template nucleic acid (under a defined ionic strength, pH and nucleic acid composition) is equilibrated and hybridized. In the present specification, a region on a target nucleic acid to which a first primer hybridizes is referred to as a first region, and a region on a target nucleic acid to which a second primer hybridizes is referred to as a second region. The relationship between the third and fourth primers will be described later in the second nucleic acid amplification step described below.

The first and second primers are preferably 5 to 50 bases long, and more preferably 10 to 40 bases long.

The concentration of the first and second primers in the reaction solution for the first nucleic acid amplification is preferably 0.05 to 2 µM, and more preferably 0.1 to 1 µM.

The first and second primers can be produced by a nucleic acid synthesis method known to those skilled in the art.

In order to allow the nucleic acid amplification reaction to proceed well, a buffer and an inorganic salt may be further added to adjust the pH and the ionic strength of the reaction solution for the first nucleic acid amplification. Examples of the buffer include Tris-HCl and the like. Examples of the inorganic salt include NaCl, KCl, and the like.

The reaction solution for the first nucleic acid amplification can be prepared by, for example, mixing a sample containing a target nucleic acid as a template, dATP, dTTP, dCTP and dGTP, first and second primers, and a DNA polymerase that selectively amplifies a nucleic acid not containing a uracil base, and an aqueous medium, a buffer and an inorganic salt as necessary. Mixing is performed by a method known to those skilled in the art such as pipetting.

The amplification reaction that can be used for the first nucleic acid amplification is not particularly limited. The amplification reaction known to those skilled in the art can be used, and polymerase chain reaction (PCR) is particularly preferably used.

The first nucleic acid amplification is preferably performed for 10 to 60 cycles, and more preferably for 15 to 50 cycles. A nucleic acid amplification reaction (hereinafter referred to as "preliminary amplification") may be performed before the first nucleic acid amplification step, and the first nucleic acid amplification step may be performed using the template. In this case, an amplification product produced by preliminary amplification is fractionated from a reaction solution of preliminary amplification. The fractionated amplification product is mixed with reagents such as polymerase and dNTPs to prepare a reaction solution, and a first nucleic acid amplification step can be performed. It is preferable that the reagents used in the preliminary amplification are the same as the reagents used in the first nucleic acid amplification step. In the case of performing preliminary amplification, the total of the number of cycles of the preliminary amplification and the number of cycles of the first nucleic acid amplification is preferably 10 to 60 cycles, and more preferably 15 to 50 cycles.

The nucleic acid amplification method of the present embodiment includes a step of performing second nucleic acid amplification using the amplification product produced in the first nucleic acid amplification step as a template. In this second nucleic acid amplification step, an amplification product containing a uracil base is produced using a primer containing a uracil base and/or dUTP and a DNA polymerase capable of amplifying a nucleic acid containing a uracil base.

The reaction solution for the second nucleic acid amplification preferably contains the amplification product produced in the first nucleic acid amplification step, third and fourth primers containing a uracil base, a DNA polymerase capable of amplifying a nucleic acid containing a uracil base, dUTP, dATP, dCTP and dGTP.

As the amplification product produced in the first nucleic acid amplification step, the reaction solution after the amplification reaction in the first nucleic acid amplification step may be used as it is or may be diluted with an aqueous medium as necessary and used. Examples of the aqueous medium include water, a phosphate buffer solution, a physiological saline solution, and the like. The amplification product produced in the first nucleic acid amplification step is adjusted to a concentration of preferably 5 to 600 fg/μl and more preferably 20 to 240 fg/μl in the reaction solution for the second nucleic acid amplification.

A DNA polymerase capable of amplifying a nucleic acid containing a uracil base can synthesize an amplification product having a base sequence containing a uracil base from a template containing a thymine base without containing a uracil base. As a DNA polymerase capable of amplifying a nucleic acid containing a uracil base, a known enzyme can be used. Examples include thermostable DNA polymerase derived from *Thermus aquaticus* and the like.

The concentration of the DNA polymerase capable of amplifying a nucleic acid containing a uracil base in the reaction solution for the second nucleic acid amplification is preferably 0.5 U/μL to 10 U/μL, and more preferably 1 U/μL to 5 U/μL.

The concentrations of dUTP, dATP, dCTP and dGTP are preferably 0.1 to 0.4 μM, and more preferably 0.2 to 0.25 μM. The reaction solution for the second nucleic acid amplification may contain dTTP. Those skilled in the art can appropriately select the dTTP concentration, in consideration of the number of thymine bases in the template nucleic acid and the like. In one embodiment, the concentration of dTTP is preferably 60% or less, and more preferably 50% or less, with the sum of dTTP content and dUTP content being 100%.

The third and fourth primers containing a uracil base used in the second nucleic acid amplification are not particularly limited as long as they are oligonucleotides that hybridize to a partial region of the first nucleic acid amplification product under stringent conditions and can be used in nucleic acid amplification. The third and fourth primers can be appropriately designed by those skilled in the art, in consideration of the relationship between the first and second primers. An amplification product containing a uracil base can be obtained in the second nucleic acid amplification step, by containing a uracil base in the primer for the second nucleic acid amplification. In the present specification, a region to which a third primer hybridizes is referred to as a third region, and a region to which a fourth primer hybridizes is referred to as a fourth region.

It is preferable that the first to fourth primers have the following relationship: (i) a part or all of the first region and the third region overlap, and a part or all of the second region and the fourth region overlap; or (ii) a part or all of the tags added to the first and second primers overlap with the third and fourth regions, respectively.

The above relationship (ii) intends to the case where the third and fourth primers are designed to hybridize to the tags attached to the first and second primers, respectively.

The third and fourth primers are designed to contain uracil bases of preferably 3 bases or more, and more preferably 5 bases or more, respectively.

The third and fourth primers are preferably 5 to 50 bases long, and more preferably 10 to 40 bases long.

The concentrations of the third and fourth primers in the reaction solution for the second nucleic acid amplification are preferably 4.0 nM to 24.4 μM, and more preferably 20 nM to 12.2 μM.

The third and fourth primers can be produced by a nucleic acid synthesis method known to those skilled in the art.

In order to allow the nucleic acid amplification reaction to proceed well, a buffer and an inorganic salt may be further added to adjust the pH and the ionic strength of the reaction solution for the first nucleic acid amplification. Examples of the buffer include Tris-HCl and the like. Examples of the inorganic salt include NaCl, KCl, and the like.

Oil may be further added to the reaction solution for the second nucleic acid amplification. Such oil-containing reaction solution is used in second nucleic acid amplification in a reaction solution containing an aqueous phase and oil, like emulsion PCR, and in this case, the amplification product produced in the first nucleic acid amplification step, the third and fourth primers containing a uracil base, a DNA polymerase capable of amplifying a nucleic acid containing a uracil base, dUTP, dATP, dCTP and dGTP, and an aqueous medium, a buffer and a salt, which are contained as necessary, form an aqueous phase. The oil is not particularly limited as long as it can be used in the method of the present embodiment, and examples thereof include mineral oils and nonionic emulsifiers (Schick, 1966), e.g., sorbitan monooleate (Span (trademark) 80; ICI), octylphenol ethoxylate (Triton (trademark) X-100) and polyoxyethylene sorbitan monooleate (Tween (trademark) 80; ICI), and the like.

The mixing ratio (volume ratio) of the aqueous phase and the oil is preferably 1 to 10 of the oil to 1 of the aqueous phase, and more preferably 2 to 8 of the oil to 1 of the aqueous phase.

The reaction solution for the second nucleic acid amplification can be prepared, for example, by mixing the amplification product produced in the first nucleic acid amplification step as a template, the third and fourth primers containing a uracil base, a DNA polymerase capable of amplifying a nucleic acid containing a uracil base, dUTP, dATP, dCTP and dGTP. Mixing is performed by a method known to those skilled in the art such as pipetting.

The amplification reaction that can be used for the second nucleic acid amplification is not particularly limited. The amplification reaction known to those skilled in the art can be used, and polymerase chain reaction (PCR), for example, digital PCR (dPCR), is particularly preferably used.

The second nucleic acid amplification is preferably performed for 10 to 70 cycles, and more preferably for 20 to 60 cycles.

The total of the number of cycles in the first nucleic acid amplification step and the number of cycles in the second nucleic acid amplification step is preferably 20 to 120 cycles, and more preferably 35 to 100 cycles.

The base sequence of the amplification product containing a uracil base obtained in the second nucleic acid amplification step is desirably a base sequence in which all thymine bases in the base sequence of the target nucleic acid are replaced with uracil bases. It is unnecessary that all thymine bases are replaced as long as amplification is suppressed in the first nucleic acid amplification step. For example, the base sequence of the amplification product containing a uracil base obtained in the second nucleic acid amplification step contains uracil bases of preferably 5 bases or more, and more preferably 10 bases or more.

In one embodiment, the second nucleic acid amplification step utilizes, for example, digital PCR using a microplate. In this embodiment, first, a reaction solution for the second nucleic acid amplification is prepared in each well of the microplate so that the amplification product produced in the first nucleic acid amplification step of one molecule per well is contained. Then, the second nucleic acid amplification is performed in the above-described conditions to acquire an amplification product containing a uracil base In one embodiment, the second nucleic acid amplification step utilizes emulsion PCR. In this embodiment, the second nucleic acid amplification step is performed, for example, by mixing an aqueous phase containing the amplification product of the first nucleic acid amplification step which is a template nucleic acid with oil to obtain a mixture, preparing an aqueous droplet containing the template nucleic acid, dATP, dUTP, dCTP, dGTP and a DNA polymerase capable of amplifying a nucleic acid containing a uracil base in an oil phase, and amplifying the template nucleic acid in the obtained droplet.

In the emulsion PCR, first, in the second nucleic acid amplification step, an aqueous phase containing the amplification product of the first nucleic acid amplification step as a template nucleic acid, third and fourth primers, dATP, dUTP, dCTP, dGTP and a DNA polymerase capable of amplifying a nucleic acid containing a uracil base are mixed with oil to obtain a mixture.

All or a part of the third and fourth primers of the reaction system may be immobilized on the beads. The beads have a diameter of, for example, about 0.1 to 10 μm. The beads are typically made of a polymeric material, such as polystyrene, and a nonpolymeric material, for example, silica can also be used. Other styrene copolymers, methyl methacrylate, functionalized polystyrene, glass, silicon and carboxylate may be contained. The particles may be superparamagnetic. Such superparamagnetic particles are easy to purify after the reaction.

The beads can be modified by covalent or noncovalent interactions with other materials to alter the overall surface characteristics, for example, hydrophobicity or hydrophilicity, or to bind molecules that impart binding specificity. Such molecules include, without limitation, antibodies, ligands, members of a specifically binding protein pair, receptors, nucleic acids or chemically active groups (for example, aldehyde or carboxy groups). Examples of the specifically binding protein pair include avidin-biotin, streptavidin-biotin, and factor VII-tissue factor.

In one embodiment, the third or fourth primer is bound to the beads by arbitrary means known in the art. The third or fourth primer can be covalently or noncovalently bound to the beads. The third or fourth primer may be bound via an intermediate, for example, via protein-protein interaction, for example, antibody-antigen interaction or biotin-avidin interaction. Other specifically binding pairs known in the art can also be used. In order to achieve optimal amplification, the primer that binds to the beads may be longer than required in a homogeneous liquid phase reaction. The length of the primer that binds to the beads need not be the same as the length of the primer liberated from the beads in the liquid phase.

Next, an aqueous droplet containing the amplification product of the first nucleic acid amplification step as a template nucleic acid, the third and fourth primers, dATP, dUTP, dCTP, dGTP and a DNA polymerase capable of amplifying a nucleic acid containing a uracil base is prepared in an oil phase. The aqueous droplet obtained here is so-called water-in-oil emulsion. The method for preparing an aqueous droplet in an oil phase is not particularly limited. For example, the aqueous droplet in an oil phase can be prepared by shaking or stirring a mixture of the aqueous phase and the oily phase by pipetting or the like, or by discharging the aqueous phase into the oily phase using a microchannel chip. In preparing the aqueous droplet in an oil phase, a multi-well plate may be used.

By mixing the aqueous phase containing a low concentration of template nucleic acid and/or beads with the oil phase, aqueous droplets can be formed so that the maximum number of the template nucleic acid molecule contained in the aqueous droplet is one and the maximum number of the beads contained in the aqueous droplet is one. Many of the droplets may be empty. A low concentration of primer bound to the beads and a high concentration of primer present in the aqueous phase and liberated from the beads may be contained in the reaction solution. The aqueous droplet has a diameter of, for example, less than 1 μm to 100 μm order, preferably 0.5 to 50 μm, and more preferably 1 to 10 μm, depending on stirring conditions, assuming them to be substantially spherical.

The mixture of the aqueous phase and the oily phase may contain an emulsifier. By adding an emulsifier, the emulsion can be stabilized. The emulsifier is not particularly limited, and examples thereof include silicone-based emulsifiers, for example, Bis-PEG/PPG-14/14 dimethicone, cyclopentasiloxane (ABIL (trademark) EM 90) or ABIL (registered trademark) WE09, and the like.

The aqueous phase preferably comprises at least 10% (v/v) or more, more preferably 20% (v/v) or more, and further preferably 40% (v/v) or more in the emulsion. Thus, the oily phase preferably comprises less than 90% (v/v), more preferably less than 80% (v/v), and further preferably at least less than 60% (v/v) in the emulsion. Here, the emulsifier constitutes an oily phase. The emulsifier occupies preferably 5% (v/v) or more, more preferably 8% (v/v) or more, and further preferably 10% (v/v) in the oily phase.

The mixture of the aqueous phase and the oily phase may further contain an auxiliary emulsifier. The auxiliary emulsifier can work together with the emulsifier to facilitate the formation and stabilization of an aqueous compartment in the emulsion. The auxiliary emulsifier is not particularly limited, and examples thereof include polyglyceryl-3 oleate or polyglyceryl-4 isostearate, and the like.

The auxiliary emulsifier preferably has a molecular weight of less than 10,000 g/mol.

Then, under the conditions of the second nucleic acid amplification defined above, the template nucleic acid in the droplet obtained above is amplified. In the case where the primer is immobilized on the beads, an amplification product immobilized on the beads is formed by the second nucleic acid amplification reaction.

When emulsion PCR using beads is performed in the second nucleic acid amplification step, the emulsion may be "broken" or disintegrated by a method known to those skilled in the art after amplification. A method of breaking the emulsion is, for example, to add a detergent. The detergent includes, but is not limited to, Triton X100, Laureth 4 and Nonidet (for example, NP-40). Preferably, the emulsion breaking solution not only provides effective phase separation but also can prevent agglomeration of the beads released from the emulsion. The emulsion breaking solution also can prevent the formation of an oily phase that cannot be easily removed by pipetting. The emulsion breaking solution may contain an alcohol, for example, 2-butanol and/or 1-propanol. The addition of alcohol can greatly enhance emulsion breaking while keeping bead agglomeration to a minimum and allowing pipetting.

The emulsion breaking solution may be used as a cleaning liquid for washing beads and/or reaction vessel to further clean the reactant. The cleaning liquid can also be used for washing the beads and/or for nucleic acid denaturation. The cleaning liquid contains, for example, 2-butanol and/or 1-propanol.

The nucleic acid amplification method of the present embodiment may further include a step of detecting an amplification product of the second nucleic acid amplification step after the second nucleic acid amplification step. In the detection step, a method generally used for detecting an amplification product of a nucleic acid can be used. For example, an intercalator (for example, SYBR (registered trademark) Green, ethidium bromide, or the like), a labeled probe containing an oligonucleotide that hybridizes to the amplification product and a labeling substance and the like are used. As the labeled probe, for example, a probe to which a fluorescent substance is bound, a probe to which a fluorescent substance and a quencher which quenches fluorescence are bound (for example, TaqMan (registered trademark) probe) or the like can be used. In the case of detecting a mutation of a gene in a sample, nucleic acid amplification is performed by, after the second nucleic acid amplification step, detecting a mutant amplification product, using a labeled oligonucleotide probe that specifically hybridizes to the mutant-type amplification product of the second nucleic acid amplification step and a labeled oligonucleotide probe that specifically hybridizes to a wild-type amplification product of the second nucleic acid amplification step.

The nucleic acid amplification method of the present embodiment does not require enzymatic degradation treatment of a nucleic acid containing a uracil base. In the case where the sample is vigorously stirred during preparation or breaking of the emulsion, nucleic acid molecules may aerosolize and scatter in the air. In such a case, carryover tends to occur, and the method of the present embodiment is particularly preferable.

The scope of the present disclosure also encompasses nucleic acid amplification reagents used in the above method.

The form of the nucleic acid amplification reagent is not particularly limited, and may be solid (for example, powder, crystal, freeze-dried product, or the like) or liquid (for example, solution, suspension, emulsion, or the like). It is preferable that constituents of the nucleic acid amplification reagent are stored in separate containers or individually packaged. The nucleic acid amplification reagent may be provided with a labeled oligonucleotide probe for detection, and in this case, the labeled oligonucleotide probe may be immobilized on a solid phase. The details of the DNA polymerase that selectively amplifies a nucleic acid not containing a uracil base, the DNA polymerase capable of amplifying a nucleic acid containing a uracil base, dATP, dTTP, dUTP, dCTP and dGTP, the labeled oligonucleotide probe and the solid phase are the same as those described in the description of the nucleic acid amplification method.

In the first present embodiment, a container storing the above-described various reagents may be packed in a box and provided to the user. This box may contain a package insert of the nucleic acid amplification reagent. For example, the constitution of the nucleic acid amplification reagent, the nucleic acid amplification protocol and the like are preferably described in this package insert. FIG. 1A shows an example of the external appearance of the nucleic acid amplification reagent of the present embodiment. In the figure, reference numeral 110 denotes a nucleic acid amplification reagent, 111 denotes a first container storing a DNA polymerase which selectively amplifies a nucleic acid not containing a uracil base, 112 denotes a second container storing dATP, dTTP, dCTP and dGTP, 113 denotes a package insert, and 114 denotes a packing box.

Figure 1B:
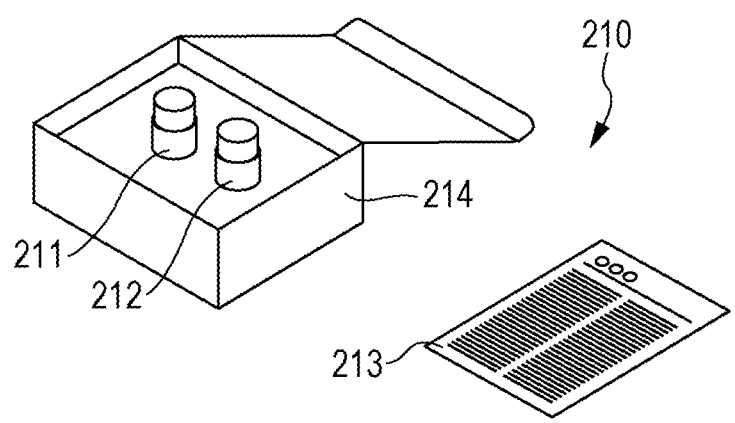
FIG. 1B is a diagram showing an example of the external appearance of a reagent of the present embodiment.

FIG. 1B shows an example of the appearance of the nucleic acid amplification reagent of the second embodiment. In the figure, reference numeral 210 denotes a nucleic acid amplification reagent, 211 denotes a first container storing a DNA polymerase capable of amplifying a nucleic acid containing a uracil base, 212 denotes a second container storing dATP, dUTP, dCTP and dGTP, 213 denotes a package insert, and 214 denotes a packing box.

Figure 1C:
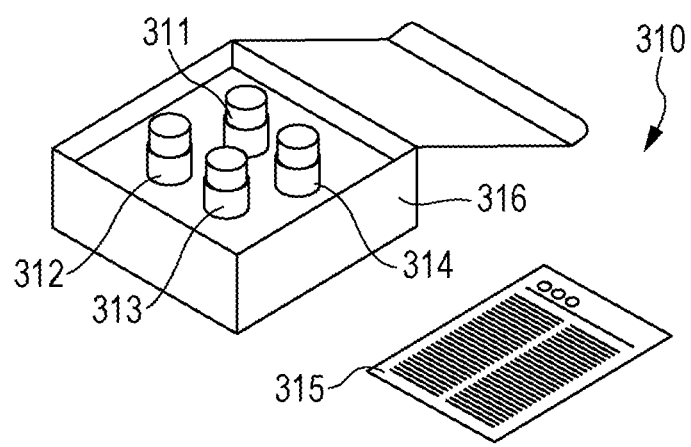
FIG. 1C is a diagram showing an example of the external appearance of a reagent of the present embodiment.

FIG. 1C shows an example of the appearance of the nucleic acid amplification reagent of the third embodiment. In the figure, reference numeral 310 denotes a nucleic acid amplification reagent, 311 denotes a first container storing a DNA polymerase that selectively amplifies a nucleic acid not containing a uracil base, 312 denotes a second container storing dATP, dTTP, dCTP and dGTP, 313 denotes a third container storing a DNA polymerase capable of amplifying a nucleic acid containing a uracil base, 314 denotes a fourth container storing dATP, dUTP, dCTP and dGTP, 315 denotes a package insert, and 316 denotes a packing box.

Hereinafter, the present invention will be described in detail with reference to examples, but is not limited to these examples.

EXAMPLES

Example 1: Preparation of DNA Fragment Containing Uracil Base (1) Preparation of PCR Reaction Solution A PCR reaction solution having the following composition was prepared: 12.5 µl 10×PCR buffer, 12.5 µl 100 mM $MgCl_2$, 2.5 µl, 1 µl primers 1 and 2 (10 µM), 0.5 µl template (7 pg/µl), 89.5 µl distilled water, 2.5 µl dNTPs (10 mM: dUTP, dGTP, dATP, dCTP, respectively), 2.5 µl Taq DNA polymerase (Peqlab: cat01-1020). The template is 500 copies of mutant DNA. The base sequence of one strand of the template is represented by SEQ ID NO: 1, and the other strand forming a double strand (dUTP-containing KRAS DNA fragment) together with the strand of SEQ ID NO: 1 is represented by SEQ ID NO: 2. Primers 1 and 2 are represented by SEQ ID NOs: 3 and 4.

(2) PCR Cycle

The PCR reaction was performed in the following number of cycles: 94° C. for 2 min, 94° C. for 10 sec→68° C. for 1 min→70° C. for 10 sec, 3 times, 94° C. for 10 sec→59° C. for 1 min→70° C. for 10 sec, 40 times, 70° C. for 2 min→left at 4° C.

(3) BEAMing

The basic method of pre-PCR reaction was performed as described in "Thermal cycle" of Nature Methods Vol. 3 No. 7 Jul. 2006.

Emulsion PCR was performed as described in Nature Methods Vol. 3 No. 7 July 2006.

Refer to paragraphs [0079] and [0080] of EP 2 315 849 B for emulsion breaking and hybridization process method.

Flow cytometric analysis was performed using the flow cytometry system described in paragraph [0081] of EP 2 315 849 B.

More specifically, these experiments were performed as described in the following (4) to (8).

(4) Pre-PCR

Wild-type KRAS DNA samples (SEQ ID NO: 5: KRAS DNA or the like mixed in water) having a mutation rate of 0, 0.1 and 1% and DNA samples prepared by adding a KRAS DNA fragment containing dUTP (double bond strand DNA composed of SEQ ID NO: 1 strand and SEQ ID NO: 2 strand) to the above samples in an amount corresponding to 1% were used for the experiment.

Pre-PCR was performed with 50 μl of a PCR reaction solution (containing approximately 1×10$^6$ molecules of template nucleic acid). Each reaction was consisted of 5× Phusion™ high fidelity buffer, 0.8 μl of Phusion™ Hot Start High-Fidelity DNA Polymerase or Phusion™ U (both NEB), 0.2 μl primer 1, 0.2 μM primer 2, each 0.25 mM dNTPs (dATP, dTTP, dGTP, dCTP), and 0.5 mM MgCl$_2$.

PCR products were quantified using the Pcogreen ds assay kit (Invitrogen). Fluorescence intensity was quantified using a fluorescent plate reader (Safire2 TECAN) using a DNA reference standard.

TABLE 1

Pre-PCR Thermal cycle

| Temperature | Time | Number of cycles |
|---|---|---|
| 98° C. | 1 min | — |
| 98° C. | 10 sec | 3 |
| ⇒70° C. | 10 sec | |
| ⇒72° C. | 10 sec | |
| 98° C. | 10 sec | 3 |
| ⇒67° C. | 10 sec | |
| ⇒72° C. | 10 sec | |
| 98° C. | 10 sec | 3 |
| ⇒64° C. | 10 sec | |
| ⇒72° C. | 10 sec | |
| 98° C. | 10 sec | 31 |
| ⇒61° C. | 10 sec | |
| ⇒72° C. | 10 sec | |
| 72° C. | 15 sec | — |

(5) Emulsion PCR

Using the amplification product of the pre-PCR step as a template, an emulsion was formed using oil and emulsion PCR master mix, and emulsion PCR was performed in a thermal cycler. The amplification product of the pre-PCR step was diluted to about 18 pg, and 150 μL of PCR master mix containing 4.0 units of Platinum Taq DNA polymerase (Invitrogen), 1×PCR buffer (NEB), each 0.2 mM dNTPs (dATP, dUTP, dGTP, dCTP), 5 mM MgCl$_2$, 0.05 μM tag 1 (emulsion PCR primer; SEQ ID NO: 6), 8 μM tag 2 (emulsion PCR primer; SEQ ID NO: 7) and about 5 to 8 million magnetic beads coated with tag 1 (Myone, Invitrogen) was prepared. 150 μL of PCR master mix and 600 μL of oil/emulsifier mix (7% ABIL WE09, 20% mineral oil, 73% Tegosoft DEC (Degussa Goldschmidt Chemical Company, Hopewell, Va.) were added to a 96 deep-well plate.

The emulsion was prepared by stirring the plate in a TissueLyser (Qiagen) at 15 Hz for 10 sec and then at 17 Hz for 7 sec. The emulsion was dispensed into another 96-well deep well plate. The 96-well deep well plate was placed in a thermal cycler under the following conditions.

TABLE 2

| Temperature | Time | Number of cycles |
|---|---|---|
| 94° C. | 2 min | 1 |
| 98° C. | 15 sec | 3 |
| ⇒64° C. | 45 sec | |
| ⇒72° C. | 75 sec | |
| 98° C. | 15 sec | 3 |
| ⇒61° C. | 45 sec | |
| ⇒72° C. | 75 sec | |
| 98° C. | 10 sec | 3 |
| ⇒58° C. | 45 sec | |
| ⇒72° C. | 75 sec | |
| 98° C. | 10 sec | 50 |
| ⇒57° C. | 45 sec | |
| ⇒72° C. | 75 sec | |

(6) Emulsion breaking

150 μL of an emulsion breaking buffer (10 mM Tris-HCl (pH 7.5), 1% Triton-X 100, 1% SDS, 100 mM NaCl, 1 mM EDTA) was added to each well, and the mixture was mixed with a TissueLyser at 20 Hz for 20 sec. The beads were recovered by rotating the suspension at 3,200 g for 2 min and removing the oil phase. The emulsion breaking process was repeated twice. All beads were collected from 8 wells and integrated. The integrated beads were washed with 150 μL of washing buffer (20 mM Tris-HCl (pH 8.4), 50 mM KCl). The amplification product on the beads was denatured with a 0.1 M NaOH aqueous solution for 5 min. Finally, the beads were washed with 150 μL of washing buffer. The washed beads were redispersed in 150 μL of washing buffer.

(7) Hybridization

Fluorescently labeled probes complementary to mutant-type and wild-type DNA sequences were designed. The size of the probes is about 15 bp to 18 bp depending on the GC content of the target region. Mutant probes were synthesized using Cy5 (trademark) phosphors on the 5' end, and wild-type probes were bound to Cy3 (trademark) phosphors (Integrated DNA Technologies). The resulting probes were used to label the amplified product extended as a positive control at a location separate from the probe recognition site in the amplification product (universal). This amplification product-specific probe was synthesized using ROX (trademark) phosphor attached to its 5' end. Probe sequences are described below. Specific hybridization reaction solutions with each region contained beads present in 30 μL of washing buffer (see emulsion breaking), 66 μL of 1.5× hybridization buffer (4.5 M tetramethylammonium chloride, 75 mM Tris-HCl (pH 7.5), 6 mM EDTA) and a mixture of mutant-type, wild-type, and universal probes prepared to 5 μM in 4 μL of TE buffer. The hybridization mixture was heated to 70° C. for 10 sec and slowly cooled to 35° C. (0.1° C./sec). After incubation at 35° C. for 2 min, the mixture was cooled to room temperature (0.1° C./sec). The beads were magnetically collected using magnet, and the supernatant containing unbound probe was removed using a pipette. The beads were resuspended in 100 μL of 1× hybridization buffer and heated to 48° C. for 5 min to remove the unbound probe. After the heating step, the beads were again magnetically collected by magnet, and the collected beads were washed once with 100 μL of washing buffer. At the final step, the supernatant was removed, and the beads were resuspended in 200 μL of TE buffer for flow cytometric analysis.

(8) Flow Cytometric Analysis

A flow cytometry system equipped with a high-throughput autosampler (BD Bioscience) was used for analysis of mutant-type and wild-type beads. Beads not containing an extension product were excluded from the analysis. For flow cytometric analysis, FCS Express 4 (De Novo software) was used.

(9) Probe Sequence

The one described in "KRAS G38A" in FIG. 10B of EP 2 315 849 B was used.

Results

Figure 2A:
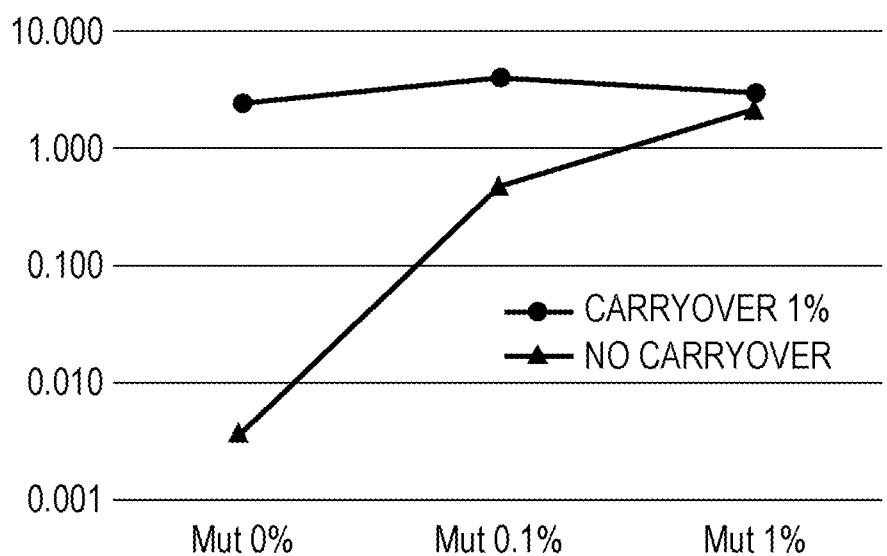
FIG. 2A is a graph showing results of mutation rate measurement in the case of using Phusion™ U in the first nucleic acid amplification.

In order to confirm that the sample contained a pseudo carryover nucleic acid, BEAMing using a PCR enzyme (Phusion™ U) capable of using dUTP as a substrate in a line similar to Phusion™ Hot Start High-Fidelity DNA Polymerase was performed in parallel. When using Phusion™ U for pre-PCR, the mutation rate was abnormal, exceeding 1% under all conditions. From this fact, it could be confirmed that the sample used for performance confirmation this time contained an appropriate carryover nucleic acid (FIG. 2A).

Figure 2B:
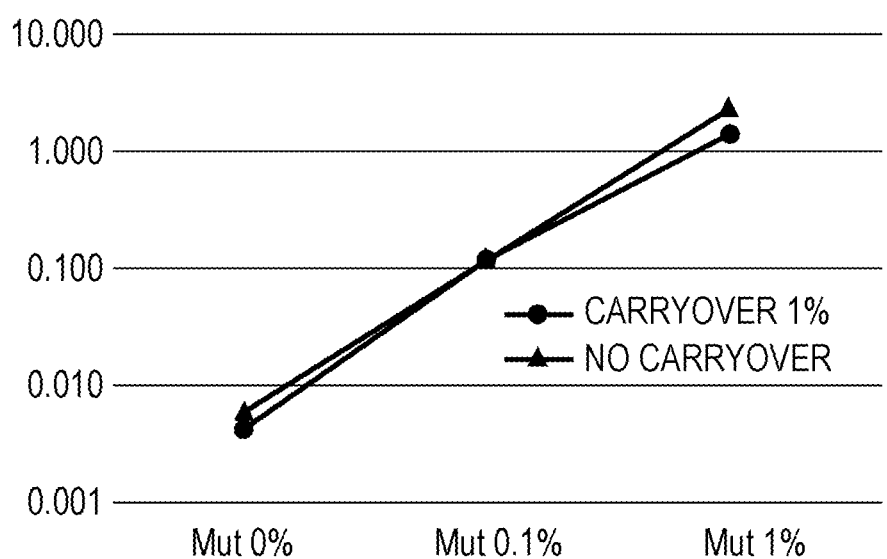
FIG. 2B is a graph showing results of mutation rate measurement in the case of using Phusion™ Hot Start High-Fidelity DNA Polymerase in the first nucleic acid amplification.

On the other hand, when using Phusion™ Hot Start High-Fidelity DNA Polymerase for pre-PCR, the mutation rate was 0.01% or less for samples with 0% mutation rate, and the mutation rate was around 0.1% for samples with 0.1% mutation rate, regardless of carryover (FIG. 2B). Therefore, when using Phusion™ Hot Start High-Fidelity DNA Polymerase for pre-PCR, it could be confirmed that the influence of contamination of uracil-containing DNA derived from the amplification product of emulsion PCR could be eliminated even without adding a uracil-containing nuclease.

Example 2

As in Example 1, BEAMing was performed using a KRAS DNA sample prepared so that the mutation rate was 0%, 1%, or a sample in which uracil-containing DNA was added to the same sample.

The dUTP-containing DNA was prepared by the same method as in Example. Pre-PCR was performed with 50 μl of a PCR reaction solution. The composition of each reaction solution is as follows: Phusion™ U: 5× Phusion™ high fidelity buffer, 0.8 ul of Phusion™ U (both NEB), 0.2 μM primer 1, 0.2 μM primer 2, 0.25 mM each dNTP, and 0.5 mM MgCl$_2$; KOD Plus neo: 10× buffer, 0.8 ul of KOD Plus neo, 0.2 μM primer 1, 0.2 μM primer 2, 0.2 mM each dNTP, 1.5 mM MgSO4.

The PCR conditions are the same as in Example 1. The conditions of emulsion PCR to flow cytometric analysis are also the same as in Example 1.

Figure 3A:
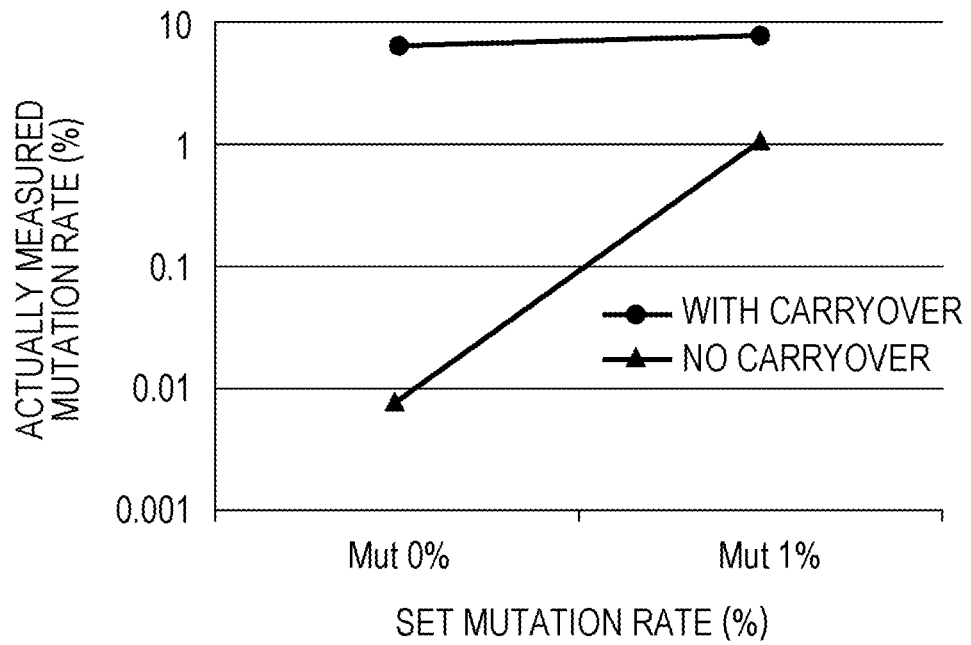
FIG. 3A is a graph showing results of mutation rate measurement in the case of using Phusion™ U in the first nucleic acid amplification.
Figure 3B:
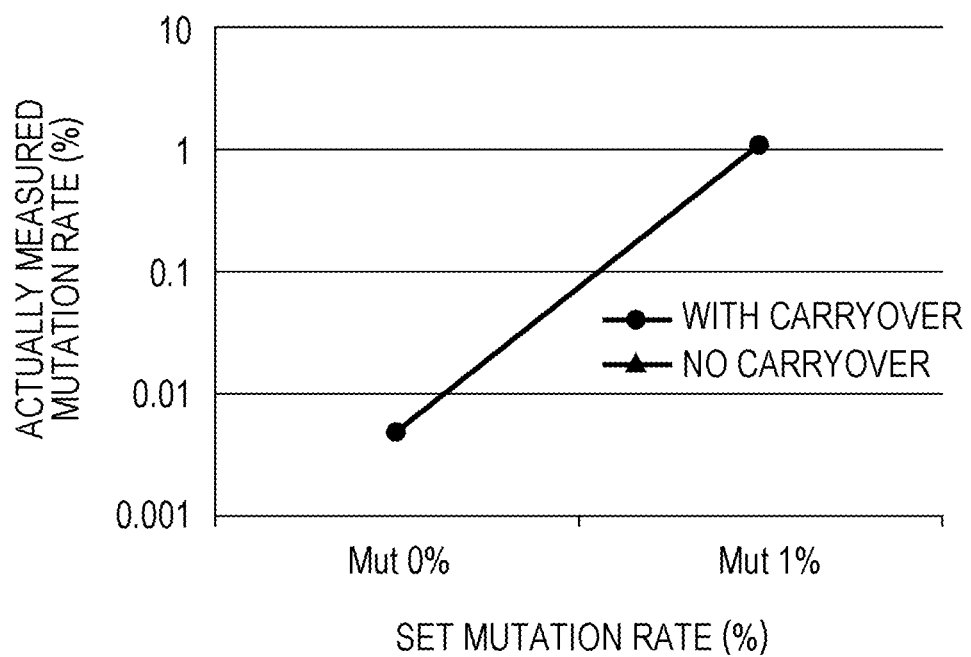
FIG. 3B is a graph showing results of mutation rate measurement in the case of using KOD plus neo in the first nucleic acid amplification.

As a result, similarly to the result of Example 1, when using Phusion™ U for pre-PCR, the mutation rate was abnormal, exceeding 1% under all conditions, and the carryover nucleic acid was amplified (FIG. 3A). On the other hand, when using KOD Plus neo, as in the case of using Phusion™ Hot Start High-Fidelity DNA Polymerase in Example 1, the mutation rate was 0.01% or less for samples with 0% mutation rate, and the mutation rate was around 0.1% for samples with 0.1% mutation rate, regardless of carryover, and amplification of carryover nucleic acid was not confirmed (FIG. 3B). Based on this, it could be confirmed that even when using KOD plus neo for pre-PCR, the influence of contamination of uracil-containing DNA derived from the amplification product of emPCR could be eliminated even without adding a uracil-containing nuclease.

Example 3: Evaluation of Effect of Pseudo Carryover

According to the method described in Example 1, the PCR product obtained by emulsion PCR using various concentrations of dUTP/dTTP mixtures was diluted 1:1,000,000 with gTE (20 μg/ml glycogen in TE (pH 8)). Assuming this PCR product to be a pseudo carryover, pre-PCR was performed according to the method described in Example 1 using the above dilution. The amplification product was subjected to gel electrophoresis to acquire electrophoresis photographs, and the amplification efficiency was quantified by densitometry using ImageJ. The results are shown in Table 3 below.

TABLE 3

| | Average - Blank |
|---|---|
| T100% | 41.9 |
| T75% | 41.6 |
| T50% | 30.7 |
| T25% | 19.2 |
| T0% | 9.7 |

In Table 3 above, for example, "T75%" shows the results when using an emulsion PCR product performed using a dUTP/dTTP mixture with dTTP:dUTP=75:25. In Table 3, "average" represents the average luminance of the target area, and "blank" represents the luminance of the background. As shown in Table 3, the amplification efficiency gradually decreases from around dTTP:dUTP=50:50. From this data, it is considered that almost 100% of PCR products will contain several uracil bases as the concentration of dUTP is higher than dTTP:dUTP=60:40.

What is claimed is:

1. A nucleic acid amplification method, comprising the steps of
performing a first nucleic acid amplification using a target nucleic acid contained in a sample as a template, and
performing a second nucleic acid amplification with forward and reverse primers, using the amplification product produced in the first nucleic acid amplification step as a template,
wherein
in the first nucleic acid amplification, a DNA polymerase that selectively amplifies a nucleic acid not comprising a uracil base is used to produce an amplification product that does not comprise a uracil base, and
in the second nucleic acid amplification, (i) dUTP and/or a primer comprising a uracil base, and (ii) a DNA polymerase capable of amplifying a nucleic acid comprising a uracil base, are used to produce an amplification product, wherein said amplification product comprises double-stranded nucleic acid having uracil on both strands thereof.

2. The method according to claim 1, wherein, in the step of performing the first nucleic acid amplification,
a reaction solution is prepared by mixing the sample, dATP, dTTP, dCTP, dGTP, and the DNA polymerase that selectively amplifies a nucleic acid that does not comprise a uracil base, and
the reaction solution is a liquid sample in which dUTP is not substantially present and in which a nucleic acid that comprises a uracil base is suspected to be present as a carryover.

3. The method according to claim 1, which does not comprise a step of degrading a nucleic acid comprising a uracil base.

4. The method according to claim 1, wherein the second nucleic acid amplification is performed in the presence of dATP, dUTP, dCTP and dGTP.

5. The method according to claim 1, wherein the step of performing the second nucleic acid amplification comprises the steps of
mixing an aqueous phase comprising the amplification product of the first nucleic acid amplification with oil, and
preparing an aqueous droplet in an oil phase, the droplet comprising the amplification product of the first nucleic acid amplification as a template, dATP, dUTP, dCTP, dGTP and the DNA polymerase capable of amplifying a nucleic acid comprising a uracil base, and
amplifying the template nucleic acid in the droplet.

6. The method according to claim 1, further comprising a step of detecting an amplification product of the second nucleic acid amplification step, after the second nucleic acid amplification step.

7. The method according to claim 6, wherein, in the detection step, the amplification product is detected using an intercalator or a labeled probe that binds to the amplification product of the second nucleic acid amplification.

8. The method according to claim 1, wherein the DNA polymerase used in the first nucleic acid amplification is a DNA polymerase derived from archaebacteria.

9. The method according to claim 1, wherein the DNA polymerase used in the first nucleic acid amplification is a thermostable DNA polymerase derived from *Pyrococcus* or derived from *Thermococcus kodakaraensis*.

10. The method according to claim 1, wherein the DNA polymerase used in the second nucleic acid amplification is a thermostable DNA polymerase derived from *Thermus aquaticus*.

11. The method according to claim 1, wherein
in the first nucleic acid amplification, a first primer that binds to a first region of the target nucleic acid and a second primer that binds to a complementary strand of a second region of the target nucleic acid are used,
in the second nucleic acid amplification, a third primer that binds to a third region of the target nucleic acid and a fourth primer that binds to a complementary strand of a fourth region of the target nucleic acid are used,
the third primer and/or the fourth primer comprise a uracil base, and
a part or all of the first region and the third region overlap, and a part or all of the second region and the fourth region overlap.

12. The method according to claim 1, wherein
the first nucleic acid amplification is performed for 15 to 50 cycles, and
the second nucleic acid amplification is performed for 20 to 60 cycles.

13. A nucleic acid amplification method, comprising the steps of
performing a first nucleic acid amplification using a target nucleic acid contained in a sample as a template, and
performing a second nucleic acid amplification with forward and reverse primers, using the amplification product produced in the first nucleic acid amplification step as a template,
wherein
in the first nucleic acid amplification, a DNA polymerase that selectively amplifies a nucleic acid not comprising a uracil base is used to produce an amplification product that does not comprise a uracil base, the DNA polymerase being derived from an archaebacteria, and
in the second nucleic acid amplification, (i) dUTP and/or a primer comprising a uracil base, and (ii) a thermostable DNA polymerase derived from *Thermus aquaticus* and capable of amplifying a nucleic acid comprising a uracil base are used to produce an amplification product, wherein said amplification product comprises double-stranded nucleic acid having uracil on both strands thereof.

14. The method according to claim 13, wherein, in the step of performing the first nucleic acid amplification,
a reaction solution is prepared by mixing the sample, dATP, dTTP, dCTP, dGTP, and the DNA polymerase that selectively amplifies a nucleic acid that does not comprise a uracil base, and the reaction solution is a liquid sample in which dUTP is not substantially present and in which a nucleic acid that comprises a uracil base is suspected to be present as a carryover.

15. The method according to claim 13, which does not comprise a step of degrading a nucleic acid comprising a uracil base.

16. The method according to claim 13, wherein the second nucleic acid amplification is performed in the presence of dATP, dUTP, dCTP and dGTP.

17. The method according to claim 13, wherein, the step of performing the second nucleic acid amplification comprises the steps of mixing an aqueous phase comprising the amplification product of the first nucleic acid amplification with oil, and preparing an aqueous droplet in an oil phase, the droplet comprising the amplification product of the first nucleic acid amplification as a template, dATP, dUTP, dCTP, dGTP and the DNA polymerase capable of amplifying a nucleic acid comprising a uracil base, and amplifying the template nucleic acid in the droplet.

18. A nucleic acid amplification method, comprising the steps of performing a first nucleic acid amplification using a target nucleic acid contained in a sample as a template, performing a second nucleic acid amplification with forward and reverse primers, using the amplification product produced in the first nucleic acid amplification step as a template, and detecting an amplification product of the second nucleic acid amplification step using an intercalator or a labeled probe that binds to the amplification product of the second nucleic acid amplification, wherein in the first nucleic acid amplification, a DNA polymerase that selectively amplifies a nucleic acid not comprising a uracil base is used to produce an amplification product that does not comprise a uracil base, the DNA polymerase being derived from an archaebacteria, and in the second nucleic acid amplification, (i) dUTP and/or a primer comprising a uracil base, and (ii) a thermostable DNA polymerase derived from *Thermus aquaticus* and capable of amplifying a nucleic acid comprising a uracil base are used to produce an amplification product, wherein said amplification product comprises double-stranded nucleic acid having uracil on both strands thereof.

19. The method according to claim 18, wherein, in the step of performing the first nucleic acid amplification, a reaction solution is prepared by mixing the sample, dATP, dTTP, dCTP, dGTP, and the DNA polymerase that selectively amplifies a nucleic acid that does not comprise a uracil base, and the reaction solution is a liquid sample in which dUTP is not substantially present and in which a nucleic acid that comprises a uracil base is suspected to be present as a carryover.

* * * * *

SEQUENCE LISTING

<160> NUMBER OF SEQ ID NOS: 7

<210> SEQ ID NO 1
<211> LENGTH: 134
<212> TYPE: DNA
<213> ORGANISM: Artificial Sequence
<220> FEATURE:
<223> OTHER INFORMATION: Synthetic sequence, strand of U-containing template

<400> SEQUENCE: 1
gctggagctc tgcagctatg actgaatata aacttgtggt agttggagcu ggugacguag    60
gcaagagugc uuugacgaua cagcuaauuc agaaucauuu uguggacgaa uauggucgua        120
uuaauuucgc ggga        134

<210> SEQ ID NO 2
<211> LENGTH: 134
<212> TYPE: DNA
<213> ORGANISM: Artificial Sequence
<220> FEATURE:
<223> OTHER INFORMATION: Synthetic sequence, another strand of U-
      containing template

<400> SEQUENCE: 2
tcccgcgaaa ttaatacgac catattcgtc cacaaaatga ttcugaauua gcugutucgu        60
caaggcacuc uugccuacgu caccagcucc aacuaccaca aguuuauauu cagucauagc        120
ugcagagcuc cagc        134

<210> SEQ ID NO 3
<211> LENGTH: 45
<212> TYPE: DNA
<213> ORGANISM: Artificial Sequence
<220> FEATURE:
<223> OTHER INFORMATION: Synthetic sequence, primer for pre-PCR

<400> SEQUENCE: 3
gctggagctc tgcagctatg actgaatata aacttgtggt agttg        45

<210> SEQ ID NO 4
<211> LENGTH: 43
<212> TYPE: DNA
<213> ORGANISM: Artificial Sequence
<220> FEATURE:
<223> OTHER INFORMATION: Synthetic sequence, primer for pre-PCR

<400> SEQUENCE: 4
tcccgcgaaa ttaatacgac catattcgtc cacaaaatga ttc        43

<210> SEQ ID NO 5
<211> LENGTH: 134
<212> TYPE: DNA
<213> ORGANISM: Artificial Sequence
<220> FEATURE:
<223> OTHER INFORMATION: Synthetic sequence, template that does not
      contain U

<400> SEQUENCE: 5
gctggagctc tgcagctatg actgaatata aacttgtggt agttggagct ggtggcgtag        60
gcaagagtgc cttgacgata cagctaattc agaatcattt tgtggacgaa tatggtcgta        120
ttaatttcgc ggga        134

<210> SEQ ID NO 6
<211> LENGTH: 20
<212> TYPE: DNA
<213> ORGANISM: Artificial Sequence
<220> FEATURE:
<223> OTHER INFORMATION: Synthetic sequence, primer for emulsion-PCR

<400> SEQUENCE: 6
tcccgcgaaa ttaatacgac        20

<210> SEQ ID NO 7
<211> LENGTH: 18
<212> TYPE: DNA

```
<213> ORGANISM: Artificial Sequence
<220> FEATURE:
<223> OTHER INFORMATION: Synthetic sequence, primer for emulsion-PCR

<400> SEQUENCE: 7
gctggagctc tgcagcta                                                 18
```